United States Patent [19]

Christopher

[11] Patent Number: 4,571,241
[45] Date of Patent: Feb. 18, 1986

[54] URINARY CATHETER WITH COLLAPSIBLE URETHRAL TUBE

[76] Inventor: T. Graham Christopher, 8727 Talbot Rd., Edmonds, Wash. 98020

[21] Appl. No.: 562,094

[22] Filed: Dec. 16, 1983

[51] Int. Cl.$^4$ ............................................. A61M 25/00
[52] U.S. Cl. .................................. 604/104; 604/247; 604/282
[58] Field of Search ................. 604/104, 105, 96, 247, 604/256, 265, 280, 283, 281, 282

[56] References Cited

U.S. PATENT DOCUMENTS

| | | |
|---|---|---|
| 3,344,791 | 10/1967 | Foderick . |
| 3,394,705 | 7/1968 | Abramson . |
| 3,428,046 | 2/1969 | Remer et al. . |
| 3,598,126 | 8/1971 | Hoeltzenbein ........................ 604/282 |
| 3,605,749 | 9/1971 | Heimlich ............................. 604/247 |
| 3,670,732 | 6/1972 | Robinson ............................. 604/105 |
| 3,769,981 | 11/1973 | McWhorter . |
| 3,848,603 | 11/1974 | Throner .............................. 604/265 |
| 4,349,029 | 9/1982 | Mott . |

Primary Examiner—Stephen C. Pellegrino
Attorney, Agent, or Firm—Christensen, O'Connor, Johnson & Kindness

[57] ABSTRACT

An indwelling urinary catheter having a rigid tubular portion for holding open the entrance of the bladder and a collapsible tubular portion extending through the urethra. The collapsible tube is closed by the normal urethral mechanism and opened upon the flow of urine, thus blocking bacterial migration into the body and avoiding abnormal, continuous distention of the urethra and consequent discomfort to the patient. Avoided, as well, is the transmission of infection occasioned by the sliding motion of rigid tube catheters within the urethra.

12 Claims, 7 Drawing Figures

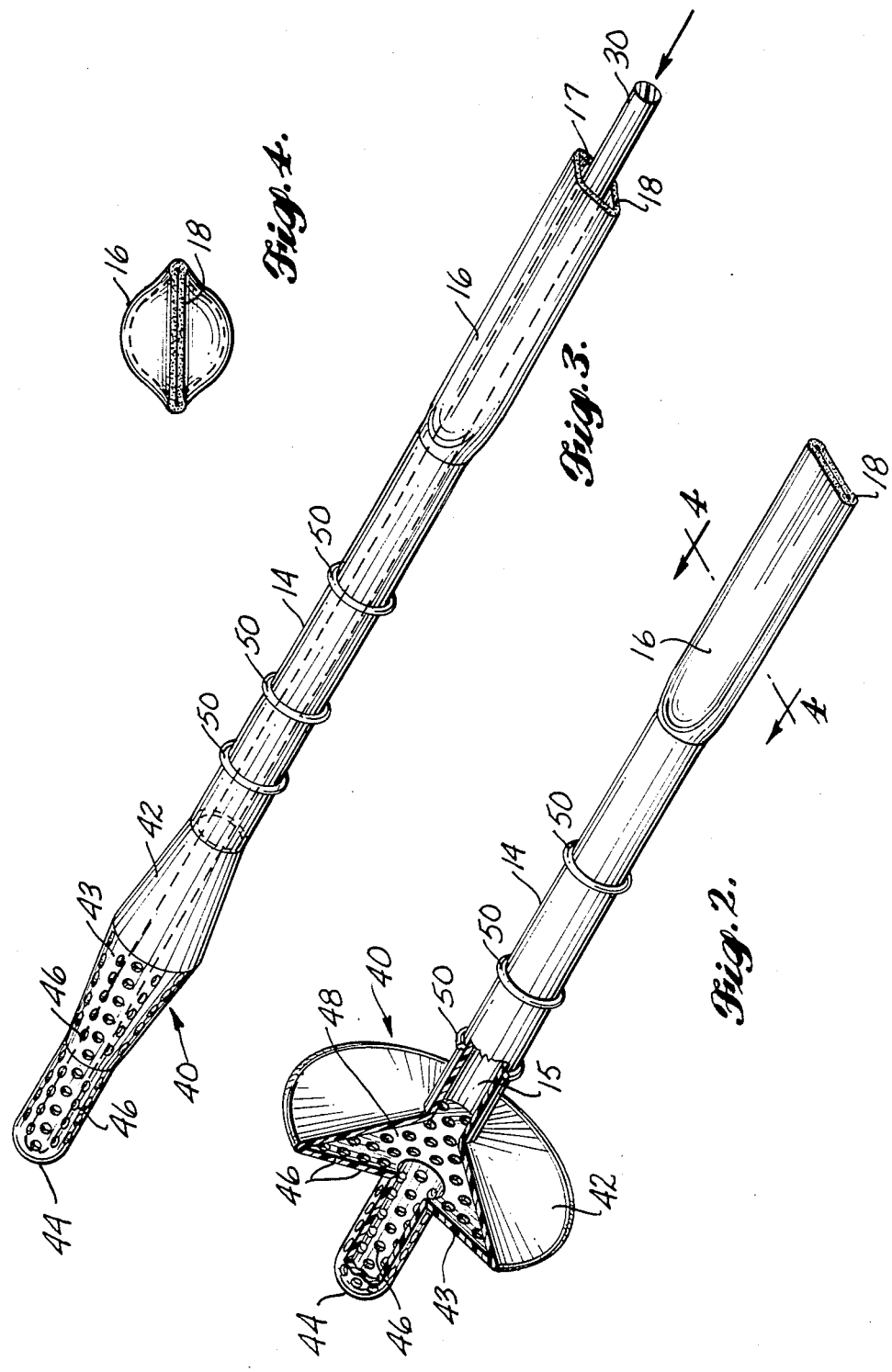

URINARY CATHETER WITH COLLAPSIBLE URETHRAL TUBE

BACKGROUND OF THE INVENTION

The present invention relates generally to urinary catheters and, more particularly, to an indwelling catheter, which permits the continuous collection of urine while reducing irritation of the urethra and diminishing the likelihoood of bacterial migration into the bladder.

In general, urinary catheters are intended to permit continuing collection of urine without leakage into a patient's clothing and bedding. To accomplish these functions, such catheters typically include means for retaining the catheter within the bladder, means for defeating the sphincter valve mechanism that normally closes the urethra, and a sterile system for transferring the collective urine to a suitable container.

The standard Foley catheter is a typical example of this type of retained urinary catheter. In simplest form, such catheters consist of a thick-walled elastic tube with an inflatable balloon at the end, which is inserted into the bladder. Although flexible enough to follow the curvature of the urethra to permit insertion, the tube is radially rigid in order to continually distend the urethra and neck of the bladder to allow continuous drainage of urine into a connected sterile tubing and container. Although effective for the intended purpose, such rigid tube catheters have several drawbacks. Normally, the urethra is a closed canal, opening only during the passage of urine, or semen in the male. This mechanism provides a barrier against the introduction of infection from outside the body into the urinary tract. The rigid-tube catheter continuously defeats this mechanism, thus increasing the incidence of infection. With normal body motion, the rigid tube also moves, chafing the urethral epithelium while also transmitting bacteria up into the bladder by a pumping/sliding action. Patient discomfort results, especially when there is a prolonged presence of the catheter.

The present invention is primarily directed to alleviation of the problems of infection and discomfort occasioned by the use of rigid-tube urinary catheters.

SUMMARY OF THE INVENTION

In accordance with the invention, there is provided a catheter that permits the continuous collection of urine without the necessity of continually distending the urethra. This is accomplished through the use of a tube having two distinct segments. To defeat the valve-like mechanism of the sphincter muscle, the catheter includes a relatively short tubular segment having walls that are sufficiently rigid to hold open the entrance into the bladder. To transfer the urine to a receiving container, a collapsible tube is connected at its distal end to the proximal end of the rigid-wall tube. When inserted, the collapsible tube extends the entire length of the urethra from a point proximally adjacent the neck of the bladder. This latter segment is readily collapsed by the normal urethral closing mechanism. Upon the flow of urine, however, the collapsible tubing is readily distended to the extent necessary to allow the urine to pass. By thus tracking the normal response of the urethra to a flow of urine, the catheter avoids the problem of bacterial transmission heretofore encountered in the use of conventional devices.

Since the collapsible segment also provides no longitudinal rigidity, the catheter does not follow the body movements of the patient, thus, avoiding the chafing problems and the longitudinal pumping effect occasioned by use of catheters having rigid-wall tubing. Because of the flexibility of the collapsible segment of the catheter, it is necessary to use a special introducer to position the catheter in the bladder. In preferred form, the introducer is a semi-rigid plastic sound, or probe, which is contained, for insertion, within the interior drainage canal of the catheter. After the catheter is in position within the bladder, the sound is removed.

In accordance with additional aspects of the invention, antibacterial seals may be provided on the rigid segment of the catheter lying outside of the bladder. For enhanced bacterial safeguarding, these seals also may be impregnated with bactericides.

According to yet another aspect of the invention, provision is made for an external seal about a portion of the catheter exiting the body. In a preferred form, the external seal forms a pocket having an access port through which bactericidal gels may be introduced as an additional safeguard.

BRIEF DESCRIPTION OF THE DRAWINGS

The invention can best be understood by the following portion of the specification taken in conjunction with the accompanying drawings in which:

FIG. 2 is a perspective view of the distal portion of the catheter showing, in partial section, the retaining head in its radially enlarged position and showing the urethral tube broken and in the collapsed condition;

FIG. 3 is a perspective view similar to FIG. 2 but showing the retaining head radially reduced by the introducer for insertion or retraction;

FIG. 4 is a front sectional view taken along line 4—4 of FIG. 3 showing the collapsible segment in both a collapsed and a partially distended position;

DETAILED DESCRIPTION OF THE PREFERRED EMBODIMENTS

Figure 1:
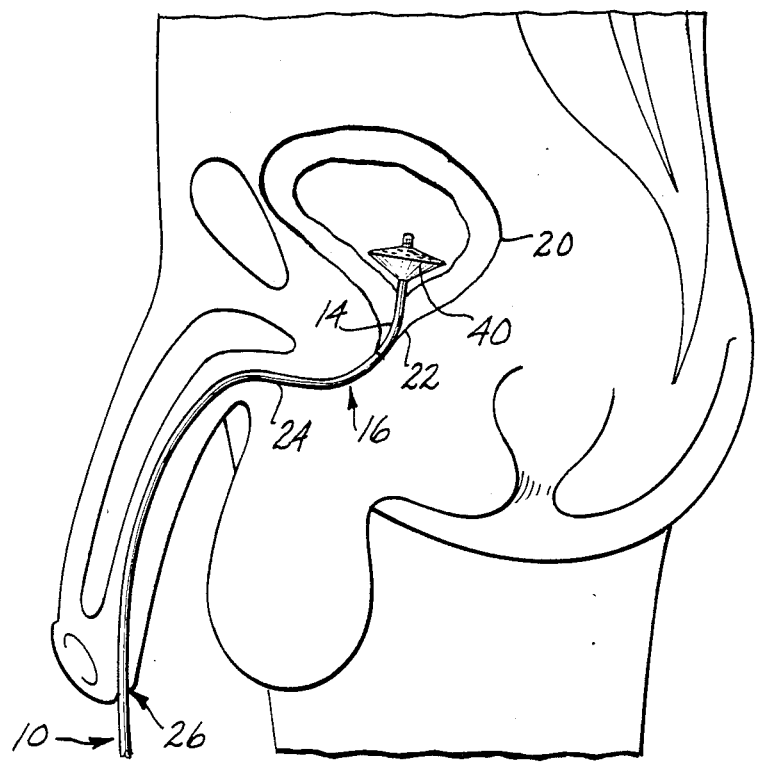
FIG. 1 diagrammatically illustrates a catheter positioned through the urethra and into the bladder.

Referring to FIG. 1, a male version of the catheter 10 of the present invention is shown secured in place within a bladder 20 by a retaining head 40. Urine is drained through an internal channel in the drainage tube portion of the catheter, which extends from retaining head 40 through the bladder neck 22 and outward of the body through the urethra 24 and urethral exit 26.

As shown in FIG. 1, but illustrated in greater detail in FIGS. 2 and 3, two distinct tubular segments constitute the portion of the catheter drainage tube extending from the bladder to the urethral exit 26. A flexible, but axially rigid bladder tube 14 is connected at its distal end to the retaining head 40 and extends from the bladder proximally through the bladder neck 22. The rigidity of bladder tube 14 defeats the valving mechanism of the sphincter, which normally closes the urethra in the area of the bladder neck 22.

A collapsible urethral tube 16 is connected at its distal end to the proximal end of the bladder tube 14. When the catheter is properly inserted, the terminus of the collapsible urethral tube, i.e., its juncture with the bladder tube, is positioned at the beginning of the urethra in the area proximally adjacent the bladder neck. Thus, except for the relatively short bladder tube-retaining head segment, the catheter is predominately nonrigid throughout its length within the body.

Both the bladder tube 14 and the urethral tube 16 have hollow interiors, or bores, 15 (FIG. 2) and 17 (FIG. 3), respectively, which are interconnected to form an open-ended drainage channel through their combined lengths. In peferred form, the radial dimensions of the bladder tube and urethral tube, as well as the radial dimension of their respective bores, substantially correspond, so that the tubular section of the catheter is substantially uniformly dimensioned both externally and internally. As will be discussed more fully hereinafter, this preferred configuration aids the insertion of the catheter and helps achieve an intended purpose of providing comfort to the patient.

In FIGS. 2 and 3, the scale relative to FIG. 1 has been enlarged and the urethral tube broken near its connection with the bladder tube for purposes of illustration. As shown, the collapsible urethral tube 16 is a relatively thin-walled structure containing a plurality of longitudinal fibers 18 (see also FIG. 4). According to a preferred construction, the urethral tube 16 has flexible walls made of a pliant material with high tensile strength fibers embedded in the walls and oriented axially about the longitudinal axis of the tube. Preferably, the fibers extend substantially the length of the urethral tube.

As a result of this construction, the urethral tube has significant longitudinal tensile strength and is resistant to outward distension beyond its normal radius dimensions. Importantly, however, the tube is readily collapsed to the position shown in FIGS. 2 and 4 by radially compressive forces. When operatively positioned, the tube 16 is, thus, collapsed by the normal closing mechanism of the urethra, thus closing the bore 17. Upon a flow of urine through the normally distended bladder tube 14, the collapsed urethral tube naturally distends to permit passage of the urine to a suitable conventional sterile collection system, not shown. Since the urethral tube distends only during the passage of urine and only to the extent necessary to allow such passage, the present catheter avoids the problems associated with continuous distension of the urethra occasioned by the use heretofore of rigid-wall catheter tubes. Specifically, the collapse of the urethral tube closes the avenue of bacterial transmission into the body and permits the urethral wall to relax rather than be abnormally and continuously distended. This reduces the incidence of bacterial infection and, as well, diminishes the likelihood of damage to the urethral wall.

The construction of the urethral tube also provides more comfort to the patient. Unlike the known rigid-tube catheters that move within the urethra in response to patient movements, the present urethral tube provides no longitudinal rigidity, i.e., it is not resistant to compression. Thus, forces on the catheter tubing external to the body are not transmitted as damaging or irritating forces on the urethral wall. Avoided, as well, is the characteristic sliding motion of rigid-tube catheters which can transmit bacteria along the urethra. It is to be noted that, while the present urethral tube is not longitudinally rigid, the longitudinal tensile strength imparted by the fibers assures that the internal rigid part of the catheter (the bladder tube) cannot become accidentally disconnected (and the entire catheter withdrawn simply by tension).

Because of the collapsing and compressing characteristics of the urethral tube, it is necessary to use a removable rigidifying introducer 30 for insertion of the catheter. This introducer 30 is configured to slide easily within the interior of the catheter and may be constructed of any suitable material that is sufficiently rigid to maintain its shape but flexible enough to follow the contours necessary for insertion. A plastic sound is an example of a suitable introducer. As shown in FIG. 3, the introducer 30 also serves to flatten the retaining head 40 for insertion or retraction of the catheter, as will be explained hereinafter.

The urethral tube 16 and longitudinal fibers 18 may be constructed of any suitable materials that exhibit the characteristics described above. For example, this tube may be constructed of an elastomeric or polymeric material (such as one containing organosilicon polymers) with embedded nylon thread. The specific dimensions of the tubing and thread, as well as the number of threads, will be dictated by the particular materials chosen. As long as the desired characteristics are achieved for the urethral tube, it is not essential that the fibers be arranged only longitudinally. It is important, however, that the urethral tube be constructed to exhibit a significant amount of tensile strength in order to withstand the stress exerted on the tube during insertion or withdrawal of the catheter. All such configurations that provide a collapsible tube that is also resistant to longitudinal tensile stress are within the purview of this invention and the appended claims.

As an optional feature, electronic body function sensors and their associated electrical interconnections may be incorporated into the structure of the urethral tube 16 for monitoring purposes. For example, temperature transducers embedded among the longitudinal fibers 18 may be interconnected with external equipment to record or indicate temperature.

The bladder tube 14 may be constructed of any suitable material, such as plastic, which will be sufficiently rigid to effect distension of the bladder opening, yet be sufficiently flexible to facilitate insertion.

To avoid the problems associated with the present balloon retaining devices, it is preferred to use a more passive means for retaining the catheter. In the preferred form, the retaining head, or retainer 40, has opposed, disk-shaped flaps 42 and 43 constructed of a resilient material that are normally retracted, or folded, in the retention mode shown in FIGS. 1 and 2. In this position, the radial dimension of retainer 40 is greater than the radial dimension of bladder tube 14. When so deployed, the proximal surfaces of flap 42 collapse against the interior walls of the bladder to retain the catheter. For draining urine, the distal faces of the flap 43 and the projecting nose 44 have openings 46 communicating with an internal chamber 48 of the retainer. The chamber 48, in turn, has connection with the drainage channel formed by the interconnected bores 15 and 17 in the bladder tube and the urethral tube, respectively.

To insert or withdraw the catheter, the introducer 30 is passed through the drainage channel and into contact with the interior surface of the projecting nose 44. When the introducer is forced distally, the flaps 42 and 43 of the retainer are flattened, thus reducing the radial dimension of the retainer 40. In FIG. 3, the flaps are shown partially flattened. For insertion or withdrawal, it is preferred that the flaps be further flattened so that the radial dimension of the retainer is about the same as the radial dimension of the bladder tube 14. Since the retainer 40 is constructed of a resilient material, when the introducer is withdrawn, the flaps return to the enlarged radial position shown in FIG. 2.

For enhanced protection against bacterial invasion, the catheter may include one or more optional internal seals. Preferably, these seals take the form of sealing rings 50 that encircle the bladder tube 14 distally of its connection with the retainer 40 as shown in FIGS. 2 and 3. Although a plurality of sealing rings is illustrated, it will be appreciated that only one seal could be employed. In addition to providing a barrier to bacteria, sealing rings 50 also help to stabilize the more rigid bladder tube portion of the catheter. For added effectiveness, the seals may optionally be coated or impregnated with a bactericide. Sealing rings constructed of a pervious material, such as plastic foam, are particularly useful for this purpose.

Figure 5:
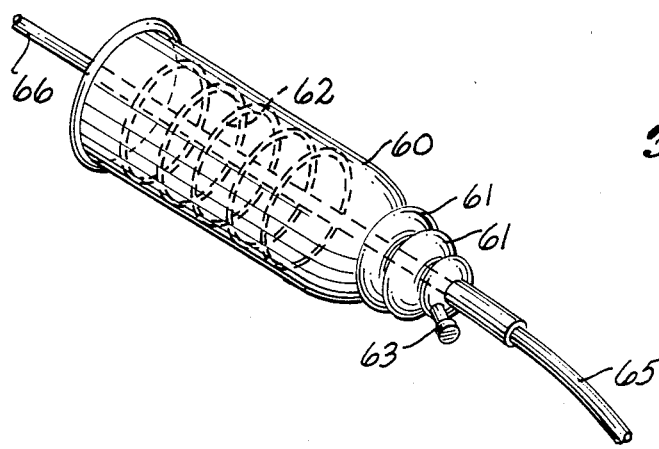
FIG. 5 is a perspective view of a male external seal for the catheter exit site.
Figure 6:
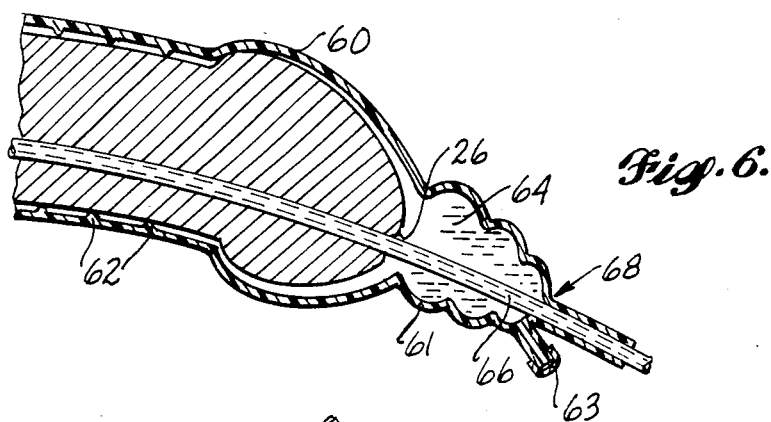
FIG. 6 is a diagrammatic illustration, in side elevational cross section, of the external seal of FIG. 4.

According to yet another aspect of the invention, an external seal is provided for the exit site of the catheter as it leaves the body. These seals have the twofold purpose of minimizing the entry of bacteria into the urethra and minimizing transmission of motion and tension on the external portion of the catheter to the portion of the catheter within the body. In general, these seals are constructed of a pliant material that will fit snugly to the skin surrounding the exit site of the catheter. As well, the seals are configured to conform to the anatomy of the exit site for a male or female patient. Referring initially to the male version illustrated in FIGS. 5 and 6, the external seal 60 has corrugations or ridges 62 (FIG. 6) at its points of contact with the body skin in order to enhance an airtight adhesion. Proximally outward from the urethral exit 26, the seal forms an internal pocket 64 which completely surrounds the portion of the catheter tube 66 as it leaves the body. Although in FIG. 6 tube 66 is shown to be a continuous tube, which, for example, could be the continuation of the collapsible urethral tube 16, it is to be understood that there could be an interconnection of the urethral tube 16 with the tubing 65 leading into the collection system (as illustrated in FIG. 5). Optionally, the junction of the interconnection also could be contained within the internal pocket 64. At its proximal end 68, the external seal 60 has a fluid-tight connection with the catheter tube 66. Extending distally from this connection, is a concertina configuration of accordian pleats, or folds, 61. In conjunction with the fluid-tight pocket 64, the accordian folds 61 function to dampen external forces applied to the catheter tube 66. For example, tension on the catheter will extend the accordian folds creating a fluid force witin the pocket 64, which will draw the external seal inwardly at its points of contact with the skin, for example, adjacent the sealing ridges 62. This effect increases the adhesion between the seal and skin, thus minimizing bacterial entry into the pocket. As well, the arrangement effects the transmission of tension on the catheter tube to the surface of the patient's body.

As an additional safeguard, bactericidal gels may be contained within the pocket 64. Such gels will prevent bacterial entry to the urethral exit 26, provide abrasion-avoiding lubrication between the seal and the skin, and enhance the establishment of a fluid-tight seal between the seal and skin. Optionally, the seal 60 may include an injection port 63 for the sterile introduction or replenishment of sealing gel within the pocket 64. Provision of the injection port prolongs the effectiveness of the external seal without risk of contamination.

Figure 7:
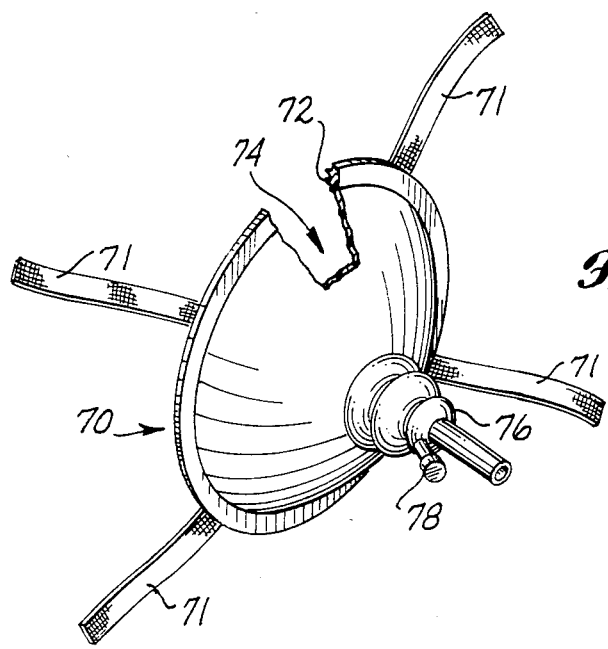
FIG. 7 is a diagrammatic perspective view of a female external seal for the catheter exit site.

The female version of an external seal 70 illustrated in FIG. 7 functions in a similar fashion to the male version just described, differing only in its configuration to conform to the female rather than the male external anatomy adjacent the urethral exit. In this regard, sealing ridges 72 functionally correspond to the ridges 62 in the male version to enhance a fluid-tight seal between the seal 70 and the skin. Identical functional correspondence is likewise found between bactericidal gel pocket 74 and pocket 64, accordian pleats 76, and pleats 61, and between injection port 78 and injection port 63. In contrast to the male embodiment of the external seal, the female version of the seal includes adhesive retaining straps 71 to assist in holding the device to the patient's body.

The present invention has been described in relation to its preferred embodiment. One of ordinary skill, after reading the foregoing specification, will be able to effect various changes and substitutions of equivalents without departing from the broad concepts disclosed herein. It is therefore intended that the protection afforded by Letters Patent granted hereon be limited only by the definition contained in the appended claims and equivalents thereof.

The embodiments of the invention in which an exclusive property or privilege is claimed are defined as follows:

1. A urinary catheter comprising:
   a urethral tube, said tube being constructed of pliant material and having longitudinal fibers therein, said fibers being oriented axially in relation to the longitudinal axis of said tube, said tube having an interior bore and being of sufficient length to extend through the urethra and out of the body from the area adjacent the bladder neck, said tube being normally collapsed within the urethra but radially distended by a flow of urine through the bore, said interior bore being closed when said tube is collapsed and open when said tube is radially distended;
   a noncollapsible bladder tube connected at its proximal end to the distal end of said urethral tube, said bladder tube having an interior bore and being of sufficient length to extend into the bladder from the area adjacent the bladder neck, the interior bores of said tubes being cooperatively connected to form a drainage channel; and
   retaining means for releasably retaining said catheter after insertion.

2. The catheter of claim 1, wherein said retaining means comprises a retaining head constructed of a resilient material, said retaining head being normally in a retracted position in which the radial dimension thereof is greater than the radial dimension of said bladder tube, said retaining head being extensible to an insertion-withdrawal position by a distally directed force applied from within said retaining head, the radial dimension of said retaining head being about equal to the radial dimension of said bladder tube in the insertion-withdrawal position.

3. The catheter of claim 2, wherein said retaining head further includes a drainage hole and an internal chamber, said hole providing a passage for the flow of urine into said chamber, said chamber being connected to said drainage channel.

4. The catheter of claim 3, further including:
an internal seal disposed about a portion of the periphery of said bladder tube and positioned adjacent the neck of the bladder when said catheter is positioned in place.

5. The catheter of claim 4, wherein said seal includes a bactericide.

6. The catheter of claim 2, further including an external seal disposed in sealing engagement about a portion of the periphery of said urethral tube outside of the body and in conforming, sealed engagement with the exterior anatomy, said seal forming a pocket about the exterior anatomy when said catheter is positioned in place.

7. A urinary catheter comprising:
a urethral tube, said tube being of a pliant material and having longitudinal fibers therein, said fibers being oriented axially in relation to the longitudinal axis of said tube, said tube having an interior bore and being of sufficient length to extend through the urethra and out of the body from the area adjacent the bladder neck, said tube being normally collapsed within the urethra but radially distended by a flow of urine through the bore, said interior bore being closed when said tube is collapsed and open when said tube is radially distended;
a noncollapsible bladder tube connected at its proximal end to the distal end of said urethral tube, said bladder tube having an interior bore and being of sufficient length to extend into the bladder from the area adjacent the bladder neck, the interior bores of said tubes being cooperatively connected to form a drainage channel;
a retaining head connected to the distal end of said bladder tube, in radial dimension of said head being variable between a retaining position in which said dimension is greater than the radial dimension of said bladder tube and an insertion-withdrawal position in which said dimension is about equal to the radial dimension of said bladder tube, said head further including a drainage hole and an internal chamber, said hole providing a passage for the flow of urine into said chamber, said chamber being connected to said drainage channel; and
an external seal disposed in sealing engagement about a portion of the periphery of said urethral tube outside of the body and in conforming, sealed engagement with the exterior anatomy, said seal forming a pocket about the exterior anatomy when said catheter is positioned in place.

8. The catheter of claim 7, further including an internal seal disposed about a portion of the periphery of said bladder tube and positioned adjacent the neck of the bladder when said catheter is positioned in place.

9. The catheter of claim 7, wherein said external seal further includes accordian folds disposed between the respective points of engagement of said seal with said urethral tube and said anatomy, said folds being extensible and distensible in response to movement of said urethral tube.

10. The catheter of claim 9, wherein said external seal further includes an injection port providing fluid access to said pocket.

11. A urinary catheter comprising:
a urethral tube, said tube being of a pliant material and having longitudinal fibers therein, said fibers being oriented axially in relation to the longitudinal axis of said tube, said tube having an interior bore and being of sufficient length to extend through the urethra and out of the body from the area adjacent the bladder neck, a portion of said tube being normally collapsed within the urethra, but radially distended by a flow of urine through the bore;
a bladder tube connected at its proximal end to the distal end of said urethral tube, said bladder tube having an interior bore and being of sufficient length to extend into the bladder from the area adjacent the bladder neck, the interior bores of said tubes being cooperatively connected to form a drainage channel;
a retaining head connected to the distal end of said bladder tube for releasably retaining said catheter after insertion, the radial dimension of said head being variable between a retaining position in which said dimension is greater than the radial dimension of said bladder tube and an insertion-withdrawal position in which said dimension is about equal to the radial dimension of said bladder tube, said head further including a drainage hole and an internal chamber, said hole providing a passage for the flow or urine into said chamber, said chamber being connected to said drainage channel; and
an external seal disposed in sealing engagement about a portion of the periphery of said urethral tube outside of the body and in conforming, sealed engagement with the exterior anatomy, said seal forming a pocket about the exterior anatomy when said catheter is positioned in place, said external seal including accordian folds disposed between the respective points of engagement of said seal with said urethral tube and said anatomy, said folds being extensible and distensible in response to movement of said urethral tube.

12. The catheter of claim 11, wherein said external seal further includes an injection port providing fluid access to said pocket.

* * * * *

UNITED STATES PATENT AND TRADEMARK OFFICE
CERTIFICATE OF CORRECTION

PATENT NO.    :    4,571,241
DATED         :    February 18, 1986
INVENTOR(S)  :    T. Graham Christopher It is certified that error appears in the above-identified patent and that said Letters Patent is hereby corrected as shown below:

Column 1, line 47, "likelihoood" should be --likelihood--

Column 3, line 11, "peferred" should be --preferred--

Column 5, line 54, "witin" should be --within--

Column 7, line 35, "in" should be --the--

Column 8, line 37, "or" should be --of--

Signed and Sealed this

Eighteenth Day of November, 1986

Attest:

DONALD J. QUIGG

Attesting Officer    Commissioner of Patents and Trademarks